United States Patent [19]

Balthasart et al.

[11] Patent Number: 5,514,251
[45] Date of Patent: May 7, 1996

[54] PROCESS FOR THE REMOVAL OF WATER FROM A SOLUTION BY AZEOTROPIC DISTILLATION AND PROCESS FOR THE PRODUCTION OF A HYDROFLUOROALKANE

[75] Inventors: Dominique Balthasart, Brussels; André Jacquemart, La Hulpe, both of Belgium

[73] Assignee: Solvay (Société Anonyme), Brussels, Belgium

[21] Appl. No.: 215,605

[22] Filed: Mar. 22, 1994

[30] Foreign Application Priority Data

Apr. 1, 1993 [BE] Belgium ............... 09300321

[51] Int. Cl.$^6$ ............................................ B01D 3/36
[52] U.S. Cl. .................. 203/14; 203/67; 252/DIG. 9; 570/178; 570/262
[58] Field of Search .................. 203/14, 67, 71; 252/DIG. 9, 67; 570/178, 262

[56] References Cited

U.S. PATENT DOCUMENTS

| | | | |
|---|---|---|---|
| 745,743 | 2/1852 | Schulze | 203/14 |
| 3,275,549 | 9/1966 | Crabb et al. | 521/26 |
| 4,209,470 | 6/1980 | Lorquet | 570/180 |
| 5,182,040 | 1/1993 | Bartlett et al. | 203/67 |

FOREIGN PATENT DOCUMENTS

| | | |
|---|---|---|
| 0003147A1 | 7/1979 | European Pat. Off. . |
| 0098341A1 | 1/1984 | European Pat. Off. . |
| 0467531A1 | 1/1992 | European Pat. Off. . |
| 83984 | 8/1971 | Germany . |
| 1135503 | 5/1989 | Japan . |
| 1139780 | 6/1989 | Japan . |
| 4026637 | 1/1992 | Japan . |
| 0707145 | 4/1954 | United Kingdom ............ 203/14 |

OTHER PUBLICATIONS

"Encyclopedia of Chemical Technology", 1978, 3rd Edition, vol. 3, pp. 361–373.
CA 112:142181.

*Primary Examiner*—Virginia Manoharan
*Attorney, Agent, or Firm*—Spencer & Frank

[57] ABSTRACT

The invention relates to binary azeotropic compositions between water and 1,1-dichloro-1-fluoroethane, 1-chloro-1, 1-difluoroethane, 1,1,1-trifluoroethane, 1,1,1,2-tetrafluoroethane, 1,1-difluoroethane or trifluoroethylene, to a process for the removal of water from solutions by azeotropic distillation using these compositions, as well as to a process for the production of a hydrofluoroalkane in which water is removed from the mixture of reaction products by azeotropic distillation using these compositions.

12 Claims, 2 Drawing Sheets

PROCESS FOR THE REMOVAL OF WATER FROM A SOLUTION BY AZEOTROPIC DISTILLATION AND PROCESS FOR THE PRODUCTION OF A HYDROFLUOROALKANE

FIELD OF THE INVENTION

TECHNOLOGY REVIEW

The invention relates to azeotropic compositions comprising water and at least one fluorohydrocarbon, to a process for the removal of water from a solution by azeotropic distillation and to a process for the production of a hydrofluoroalkane.

It is known to prepare hydrofluoroalkanes by reaction of saturated or unsaturated halogen-containing hydrocarbons with hydrogen fluoride. In this known process, a mixture of reaction products is obtained, comprising the desired hydrofluoroalkane and unreacted hydrogen fluoride, as well as, commonly, hydrogen chloride and various halogen-containing organic compounds, in particular the unreacted fraction of the halogen-containing hydrocarbon used as well as various by-products. It is then not only necessary to be able to isolate the desired hydrofluoroalkane in a substantially pure form, but it is also of prime importance for the economy of the process to be able to recycle the hydrogen fluoride and any other unconverted reactant into the fluorination reactor.

In the processes for the synthesis of hydrofluoroalkanes, splitting of the mixture of reaction products into its various constituents is carried out, at least in part, by distillation. By way of examples, there may be mentioned the documents EP-A-0,003,147 (SOLVAY) and EP-A-0,098,341 (PENNWALT) relating to the splitting of the mixture of reaction products obtained in the context of the synthesis of 1-chloro-1,1-difluoroethane by reaction between hydrogen fluoride and vinylidene chloride or 1,1,1-trichloroethane. There may also be mentioned the Patent Application EP-A-0,467,531 (I.C.I.) relating to the splitting by distillation of the mixture of reaction products obtained in the context of the synthesis of 1,1,1,2-tetrafluoroethane by reaction between hydrogen fluoride and trichloroethylene or 2-chloro-1,1,1-trifluoroethane.

In the processes for the preparation of hydrofluoroalkanes by reaction with hydrogen fluoride, the presence of water generally prejudices the smooth working of the process. Apart from a possible negative effect on the performances of the synthesis of the desired hydrofluoroalkane, the increase in the water content in the mixture of reaction products inevitably results in increased corrosion of the apparatus. In practice, however, the use of absolutely anhydrous reactants proves to be very difficult. It now appears though that, due to the strong affinity of hydrogen fluoride for water, in the case of recycling of the unreacted reactants into the synthesis reactor, the hydrogen fluoride recycled is generally accompanied by water, resulting in an increase in the water content in the "reactor-unit for separation and recycling of the hydrogen fluoride" circuit. Consequently, it appears to be necessary to remove the water present in the mixture of reaction products before recycling.

Patent DD-83984 discloses a process for the removal of water from crude tetrafluorodibromoethane by addition of methanol to the crude tetrafluorodibromoethane and distillation of a ternary azeotropic mixture consisting of tetrafluorodibromoethane, methanol and water. Such a process necessarily involves the presence of tetrafluorodibromoethane and methanol in the mixture to be dried.

Moreover, in some processes for the preparation of hydrofluoroalkanes, the unsaturated hydrocarbons present as impurities in the mixture of reaction products are difficult to separate by distillation of the desired hydrofluoroalkane, due to the fact that their boiling point is too close to that of the said hydrofluoroalkane, and they are consequently converted by chlorination into heavier saturated hydrocarbons, which may then be easily separated from the said hydrofluoroalkane. Such a chlorination operation involves the placing in contact of the mixture of reaction products, optionally already freed of some of its constituents, with chlorine, which is generally introduced in excess relative to the unsaturated hydrocarbons to be converted. It has now been observed that, under certain operating conditions, the water present in the mixture of reaction products or conveyed with the chlorine forms hydrates $Cl_2$—$H_2O$ with the chlorine. These hydrates may accumulate in solid form in the cold areas of the plant, for example in the condenser at the top of the distillation column which is intended for separating the excess $Cl_2$ from the reaction product, with a view to recycling it. Whenever there are any stoppages of the plant, these hydrates risk decomposing due to reheating of the cold areas of the plant and forming a particularly corrosive solution. Apart from the serious corrosion problems that they generate, the chlorine hydrates also risk obstructing the equipment and thereby limiting its production capacity.

Removal of water from liquid compositions by azeotropic distillation is well known and is described, for example, in "Encyclopedia of Chemical Technology", 1978, 3rd Edition, Volume 3, p. 361–373. According to this process, an entrainer, which is a compound forming an azeotrope with water, is added to the composition and the resulting solution is subsequently heated and/or placed under reduced pressure in order to evaporate the azeotrope. When the solution is subjected to distillation, the water/entrainer azeotrope is removed at the top of the distillation column.

SUMMARY OF THE INVENTION

It has now been found that some well-defined fluorohydrocarbons form azeotropes with water, which allows, under certain conditions, the water present in various solutions, in particular in mixtures of reaction products recovered during the production of hydrofluoroalkanes, to be removed, thereby avoiding the above-mentioned disadvantages during the production of hydrofluoroalkanes.

DETAILED DESCRIPTION OF THE INVENTION

Figure 1:
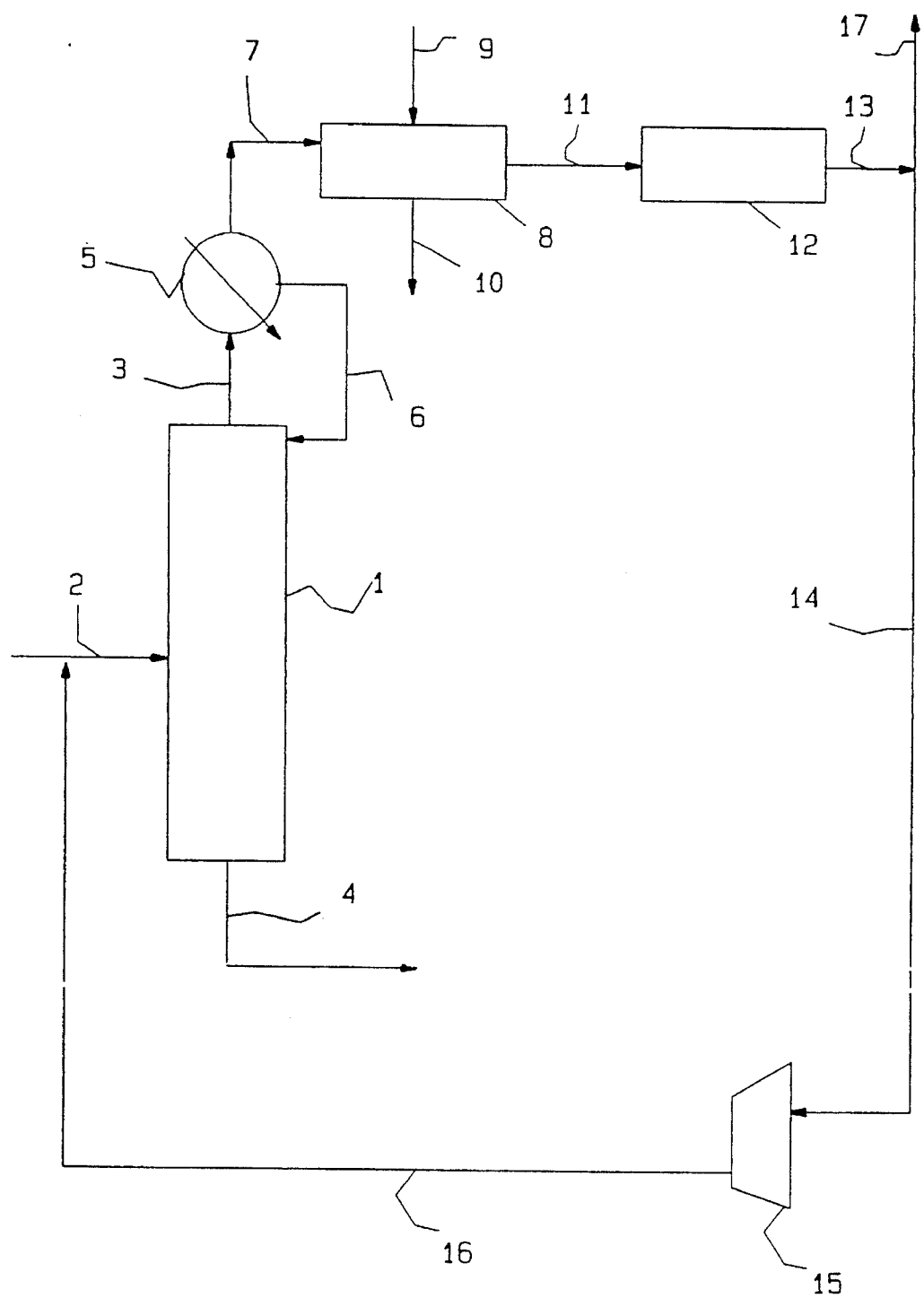
FIG. 1 illustrates a process for the manufacture of 1,1-dichloro-1-fluoroethane and 1-chloro-1,1-difluoroethane and the process may also be applied to the selective production of 1,1-dichloro-1-fluoroethane or 1-chloro-1,1-difluoroethane.

The invention consequently relates to azeotropic compositions comprising water and at least one fluorohydrocarbon selected from 1,1-dichloro-1-fluoroethane, 1-chloro-1,1-difluoroethane, 1,1-difluoroethane, 1,1,1-trifluoroethane, 1,1, 1,2-tetrafluoroethane and trifluoroethylene.

The azeotropic compositions comprising water and 1,1-dichloro-1-fluoroethane, 1-chloro-1,1-difluoroethane or 1,1,1-trifluoroethane are preferred.

The thermodynamic state of a fluid is fundamentally defined by four interdependent variables: the pressure (P), the temperature (T), the composition of the liquid phase (X) and the composition of the gaseous phase (Y). A true azeotrope is a specific system containing two or more components for which, at a given temperature and a given pressure, X is exactly equal to Y. A pseudo-azeotrope is a system containing two or more components for which, at a given temperature and at a given pressure, X is substantially equal to Y. In practice, this means that the constituents of such azeotropic and pseudo-azeotropic systems are substantially inseparable by distillation.

For the purposes of the present invention, azeotropic composition is understood to refer to a mixture of two or more constituents which has the properties of a true azeotrope or of a pseudoazeotrope, in which the molar ratio of the constituents of the mixture varies from that of the true azeotrope by no more than 10%, or for which the boiling point (at a given pressure) differs from the boiling point of the true azeotrope by no more than 0.5° C., or alternatively for which the vapour pressure (at a given temperature) differs from that of the true azeotrope by no more than 10 mbar. It is known that, in an azeotrope, the concentration of the constituents, the temperature and the vapour pressure are interdependent parameters. As soon as one of these parameters is set, the others are imposed.

Within the usual range of pressure used in the standard processes for the production of hydrofluoroalkanes, namely from 0.1 to 100 bar, the water content in the azeotropic compositions according to the invention is at least equal to 0.01 mol % and at most equal to 10 mol %. This content is most often greater than or equal to 0.1 mol %. It is preferably lower than or equal to 5 mol %.

At 20° C., the azeotropic composition essentially consisting of 1,1-dichloro-1-fluoroethane (HFA-141b) and water contains these constituents in a water/HFA-141b molar ratio equal to (4±0.4): 100. At this temperature, the vapour pressure of the azeotropic composition essentially consisting of HFA-141b and water is 0.67±0.01 bar.

At 20° C., the azeotropic composition essentially consisting of 1-chloro-1,1-difluoroethane (HFA-142b) and water contains these constituents in a water/HFA-142b molar ratio equal to (1.1±0.1): 100. At this temperature, the vapour pressure of the azeotropic composition essentially consisting of HFA-141b and water is 2.93±0.01 bar.

At 20° C. the azeotropic composition essentially consisting of 1,1,1-trifluoroethane (HFA-143a) and water contains these constituents in a water/HFA-143a molar ratio equal to (0.3±0.03): 100. At this temperature, the vapour pressure of the azeotropic composition essentially consisting of HFA-143a and water is 11±0.01 bar.

The invention is not limited to the specific compositions defined above. It is aimed at any azeotropic composition essentially consisting of water and at least one fluorohydrocarbon selected from 1,1-dichloro-1-fluoroethane, 1-chloro-1,1-difluoroethane, 1,1-difluoroethane, 1,1,1-trifluoroethane, 1,1,1,2-tetrafluoroethane and trifluoroethylene.

The azeotropic compositions according to the invention find an application in the processes for the removal of water by azeotropic distillation from solutions comprising water and at least one liquid compound other than water, such as in particular mixtures of reactant products obtained during the production of hydrofluoroalkanes.

Consequently, the invention also relates to a process for the removal of water from a solution comprising water and at least one liquid compound other than water by azeotropic distillation of a water/entrainer azeotrope, which is characterized in that the entrainer is selected from 1,1-dichloro-1-fluoroethane, 1-chloro-1,1-difluoroethane, 1,1-difluoroethane, 1,1,1-trifluoroethane, 1,1,1,2-tetrafluoroethane and trifluoroethylene.

The term entrainer is understood to denote a fluorohydrocarbon which forms with water an azeotropic composition in accordance with the invention, which composition may be removed at the top of a distillation column when the solution is subjected to distillation.

The process for the removal of water according to the present invention is particularly applicable to solutions containing a low water content, generally lower than 30% by weight. The amount of water in the solution preferably does not exceed 10% by weight of the solution. Most often, this amount does not exceed 5%. It is generally at least 5 ppm by weight. It is most often at least 50 ppm by weight.

In the process according to the invention, the entrainer generally chosen is a fluorohydrocarbon which forms with water an azeotrope, the boiling point of which is lower than the boiling point of the compound other than water present in the solution, such that the water/entrainer azeotrope is removed in the vapour state during the distillation. In a variant of the process applied in the case where the solution contains some compounds having a boiling point lower than that of the azeotrope formed by water and the entrainer, these compounds are separated from the solution with the azeotrope.

In the process for the removal of water according to the invention, the solution containing the water to be removed is subjected to a distillation step in the presence of a sufficient amount of entrainer.

The amount of entrainer necessary depends on various parameters, such as in particular its nature, the residual water content intended in the solution, the pressure and the temperature at which the distillation is carried out and the nature and the proportion of the compounds in the solution containing the water to be removed. It is normally desirable for the entrainer to be present in an amount sufficient to form an azeotrope with virtually all of the water contained in the solution. As a general rule, the amount of entrainer used is from 1 to 10 times the amount of entrainer strictly necessary in order to form the azeotrope with all of the water present in the solution. The amount of entrainer is preferably from 1.2 to 5 times the said strictly necessary amount. In a particularly preferred manner, the amount of entrainer is from 1.5 to 3 times the said strictly necessary amount.

In the process for the removal of water according to the invention, the liquid compound other than water, mentioned above, is not critical and may either be an organic compound or an inorganic compound. It may in particular contain hydracids (for example hydrogen fluoride or hydrogen chloride) or hydrocarbons which are optionally substituted, in particular by halogens (for example hydrofluoroalkanes).

The process for the removal of water according to the invention is advantageous for removing water from solutions comprising a hydrofluoroalkane as liquid compound other than water. It is particularly advantageous for removing water from solutions in which the liquid compound other than water constitutes, at least in part, the entrainer forming an azeotrope with water. In this application of the invention, the solutions containing a hydrofluoroalkane may be various compositions, such as compositions for cleaning, degreasing or drying articles, such as, for example, delicate mechanical components or optical components.

The process for the removal of water according to the invention is very particularly advantageous for removing water from mixtures of reaction products obtained during the production of a hydrofluoroalkane.

Consequently, the invention also relates to a process for the production of a hydrofluoroalkane in which there is recovered a mixture of reaction products comprising, in solution, the hydrofluoroalkane and water, the said mixture is subjected to azeotropic distillation in the presence of an entrainer which forms an azeotrope with water, and a distillate containing the azeotrope and a liquid phase containing the hydrofluoroalkane are recovered from the distillation, the process being characterized in that the entrainer is selected from 1,1-dichloro-1-fluoroethane, 1-chloro-1,1-difluorethane, 1,1-difluoroethane, 1,1,1-trifluoroethane, 1,1,1,2-tetrafluoroethane and trifluoroethylene.

The process according to the invention for the production of a hydrofluoroalkane applies to the production of any hydrofluoroalkane whose boiling point is greater than that of the abovementioned azeotrope. It in particular applies to the production of hydrofluoroalkanes containing from 2 to 6 carbon atoms and corresponding to the general formula $C_aH_bF_cX_d$ in which X denotes Cl and/or Br, preferably Cl, a is an integer from 2 to 6, b is an integer from 1 to 13, c is an integer from 1 to 13 and d is an integer from 0 to 8, with b+c+d=2a+2 when the hydrofluoroalkane is acyclic and with b+c+ d=2a when the hydrofluoroalkane is alicyclic. It applies particularly to the production of acyclic hydrofluoroalkanes corresponding to the above general formula in which X is Cl, a is an integer equal to 2, 3 or 4, b is an integer from 1 to 9, c is an integer from 1 to 9 and d is an integer from 0 to 5. It applies more particularly to the production of acyclic hydrofluoroalkanes corresponding to the above general formula in which X is Cl, a is an integer equal to 2 or 3, b is an integer from 1 to 6, c is an integer from 1 to 6 and d is an integer from 1 to 4. By way of examples, the process according to the invention is in particular applicable to the production of the hydrofluoroalkanes of formula $CH_3CCl_2F$, $CH_3CClF_2$, $CH_3CHF_2$, $CH_2CF_3$, $CH_2FCH_2F$, $CH_2FCHF_2$, $CH_2FCF_3$, $CHF_2CCl_3$, $CHF_2CF_3$, $CHCl_2CF_3$, $CHF_2CHF_2$, $CF_3CHClF$, $CF_3CF_2 CHCl_2$, $CF_2ClCF_2CHClF$, $CF_3CH_2CF_2CH_3$ and $CF_3CH_2CH_2CF_3$. The process according to the invention is very particularly applicable to the production of 1,1-dichloro-1-fluoroethane.

In the process for the production of a hydrofluoroalkane according to the invention, the hydrofluoroalkane is generally prepared by reaction of a halogen, a hydracid or hydrogen or with a saturated or unsaturated halogen-containing hydrocarbon. By way of examples of such reactions, there may be mentioned the synthesis of 1,1-dichloro-1-fluoroethane and/or of 1-chloro-1,1-difluoroethane by hydrofluorination of vinylidene chloride or of 1,1,1-trichloroethane. There may also be mentioned the synthesis of 1,1,1,2-tetrafluoroethane by catalytic hydrofluorination of a compound of formula $CX_3CH_2Cl$ or $CX_2=CHX$, with X equal to Cl or F. The operating conditions under which these reactions are carried out are well known in the prior art.

The term mixture of reaction products is understood to refer to any liquid medium containing, in the dissolved state, water, the hydrofluoroalkane to be produced and, optionally, additional substances such as, for example, unconverted reactants, by-products and impurities. This may either be a crude mixture, recovered immediately on conclusion of the synthesis, defined above, of the hydrofluoroalkane and containing additional substances, or a mixture which has, at least in part, been purified from the said additional substances.

Besides the desired hydrofluoroalkane, the mixture of reaction products generally contains other hydrofluoroalkane by-products from the synthesis or, when the desired hydrofluoroalkane is obtained from another hydrofluoroalkane, an unconverted fraction of this starting hydrofluoroalkane. It may contain at least one hydracid, such as hydrogen fluoride or hydrogen chloride. It frequently contains hydrogen fluoride. It may contain a halogen, such as chlorine or fluorine. In addition, it generally contains various halogen-containing compounds, which may be unconverted reactants from the synthesis step or by-products of the latter. It may also contain, in the dissolved state, various inorganic compounds used in the synthesis, either as inert gas, such as nitrogen, or as reactant, such as hydrogen.

The water content in the mixture of reaction products may vary within wide limits while, nevertheless, remaining lower than the hydrofluoroalkane content in the mixture of reaction products. It generally does not exceed 5% by weight of the mixture of reaction products. The process according to the invention is particularly suited to the removal of water which is present in small amounts, for example when the water content in the mixture of reaction products is between 5 and 5000 ppm by weight. The mixture of reaction products typically contains such water contents when the reactants used in order to synthesize the hydrofluoroalkane contain of the order of 10 to 500 ppm of water.

In the process for the production of a hydrofluoroalkane according to the invention, the distillation may be carried out in any standard distillation column. As the azeotrope is of the minimum boiling point type, it is recovered at the top of the column, in the distillate. The mixture of reaction products, freed from the water which it contained, is recovered at the foot of the column, in the liquid phase. This liquid phase contains the hydrofluoroalkane to be produced. It generally also comprises at least some of the additional substances defined above. Where appropriate, in order to separate these additional substances from the hydrofluoroalkane, the liquid phase of the distillation is subjected to a standard operation of separation into its constituents with a view to isolating, in a substantially pure form, the desired hydrofluoroalkane. The additional substances separated may be recycled in the most suitable manner, depending on their nature and their role in the synthesis of the hydrofluoroalkane to be produced. Distillation of the water/entrainer azeotrope is preferably carried out in a distillation column which simultaneously performs the separation of other constituents of the mixture of reaction products which have a volatility close to that of the azeotrope used.

As a general rule, the amount of entrainer present in the mixture of reaction products subjected to distillation is from 1 to 10 times the amount strictly necessary to form the azeotrope with the water present in the mixture of reaction products. The amount of entrainer present in the mixture of reaction products is preferably from 1.2 to 5 times the said strictly necessary amount. In a particularly preferred manner, the amount of entrainer present in the mixture of reaction products is from 1.5 to 3 times the said strictly necessary amount.

In a first embodiment of the process according to the invention for the production of a hydrofluoroalkane, the entrainer used is a constituent of the mixture of reaction products. It may be a reactant which has not been entirely converted in the synthesis of the desired hydrofluoroalkane. It may be a by-product formed during the synthesis. It may also be the desired hydrofluoroalkane. In this latter case, the conditions of the distillation are controlled such that only the amount of hydrofluoroalkane necessary to remove the water is recovered in the distillate, the remaining amount, preferably the majority, of the hydrofluoroalkane leaving the distillation column in the liquid phase of the distillation. This first embodiment of the process according to the invention has the advantage of avoiding any recourse to a compound which is external to the process. It is, however, only possible when one of the constituents of the mixture of reaction products forms with water an azeotrope with a boiling point lower than that of the hydrofluoroalkane to be produced and when it is present in the mixture in a sufficient amount to make it possible to remove a satisfactory amount of the water contained in this mixture.

In a second embodiment of the process according to the invention for the production of a hydrofluoroalkane, at least a part of the entrainer is added to the mixture of reaction products. Such an embodiment is necessary when the mixture of reaction products does not contain fluorohydrocarbons which form an azeotrope with water as defined above, or contains them in an insufficient amount. This addition into the reaction mixture may be carried out before subjecting it to distillation or the entrainer may be introduced directly into the distillation column.

After distillation, the azeotrope may, where appropriate, be separated from the other constituents of the distillate by any suitable method. It is also possible to split the water/entrainer azeotrope into its constituents, for example by drying using desiccant substances, or alternatively by phase separation when the azeotrope is a heteroazeotrope, as is the case for the compositions 1,1-dichloro-1-fluoroethane/water and 1-chloro-1,1-difluoroethane/water. This a splitting of the azeotrope is desirable when it is wished to recover the fluorohydrocarbon used as entrainer. This is especially the case when the fluorohydrocarbon is a reactant involved in the synthesis of the desired hydrofluoroalkane or a compound deliberately introduced into the mixture of reaction products with a view to forming the azeotrope with water. It is then preferably recycled into the hydrofluoroalkane production plant at the most suitable point depending on its function. When the entrainer is the desired hydrofluoroalkane, depending on whether the hydrofluoroalkane fraction removed in the distillate is of a more or less considerable size, a step of recovery of the water/hydrofluoroalkane azeotrope is or is not carried out, followed by a step of separation of the water and the hydrofluoroalkane, in order to recover the hydrofluoroalkane fraction which has passed into the distillate.

The invention will now be illustrated with reference to the appended figures, which schematically represent the flow diagrams of two specific embodiments of the process according to the invention for the production of a hydrofluoroalkane. These examples are given by way of illustration and are not intended to limit the invention to these specific applications.

The process outlined in FIG. 1 is intended for the joint manufacture of 1,1-dichloro-1-fluoroethane and 1-chloro-1,1-difluoroethane. To this end, hydrogen fluoride and vinylidene chloride are reacted in a reactor (not shown) and a mixture of reaction products is recovered from the reactor, typically comprising from 2.5 to 60 mol % of 1,1-dichloro-1-fluoroethane, from 2.5 to 60 mol % of 1-chloro-1,1-difluoroethane, from 30 to 90 mol % of hydrogen fluoride, from 5 to 50 mol % of hydrogen chloride, from 50 to 250 ppm of water and, where appropriate, 1,1,1-trifluoroethane (up to 5 mol %). The reaction mixture, denoted by the reference number (2), is introduced in liquid form into a distillation column (1), optionally with a supplement of 1,1,1-trifluoroethane by way of entrainer as defined above. The amount of supplementary 1,1,1-trifluoroethane is controlled such that, in the mixture subjected to distillation, the molar ratio between the 1,1,1-trifluoroethane flux and the reaction mixture flux is conventionally from 0.2 to 10%. The distillation column is maintained at a pressure of 8 to 20 bar. The distillate leaving the column via the pipe (3) mainly comprises hydrogen chloride, the water/1,1,1-trifluoroethane azeotrope and the optional excess 1,1,1-trifluoroethane.

It additionally contains nitrogen. After partial condensation in a condenser (5), the condensed part of the distillate (6) is returned to the column as reflux and the non-condensed part of the distillate (7) is sent into an absorption column (8). In the latter, the hydrogen chloride is separated from the distillate by absorption in the water introduced at (9). The hydrogen chloride and the water are removed via the pipe (10). The residual gaseous flux (11), mainly containing a mixture of 1,1,1-trifluoroethane and inert gases saturated with water, is subsequently brought to a dryer (12) in order to remove the water. In the dryer (12), the gaseous flux (11) may, for example, pass through beds of adsorbent material. The gas (13) recovered from the dryer (12) consists almost exclusively of 1,1,1-trifluoroethane and inert gases. It is sent via the pipe (14), the compressor (15) and the pipe (16) to the distillation column (1). The pipe (17) constitutes a purge, via which the inert gases such as nitrogen and, optionally, the excess 1,1,1-trifluoroethane are removed. A liquid phase (4) is recovered at the foot of the distillation column. This liquid phase conventionally contains 1,1-dichloro-1-fluoroethane and 1-chloro-1,1-difluoroethane as co-products, unreacted vinylidene chloride and hydrogen fluoride and less than 10 ppm of water. This liquid phase may be split into its various constituents in a known manner, so as to recover the 1,1-dichloro-1-fluoroethane and the 1-chloro-1,1-difluoroethane, it being possible for the unconverted reactants (vinylidene chloride and hydrogen fluoride) to be subsequently recycled into the hydrofluorination reactor. In a standard variant of the process outlined in FIG. 1, a part of the liquid phase (4) is evaporated in a distillation vessel and sent in vapour form into the column (1).

This first embodiment illustrates that the process according to the invention proves to be particularly advantageous when the hydrogen fluoride used as reactant is used in an excess amount relative to the stoichiometric amount and when, for obvious economic reasons, it is desired to recycle this excess hydrogen fluoride in anhydrous form. The process in accordance with the invention, which has just been described with reference to FIG. 1, may be applied to the selective production of 1,1-dichloro-1-fluoroethane or 1-chloro-1,1-difluoroethane.

Figure 2:
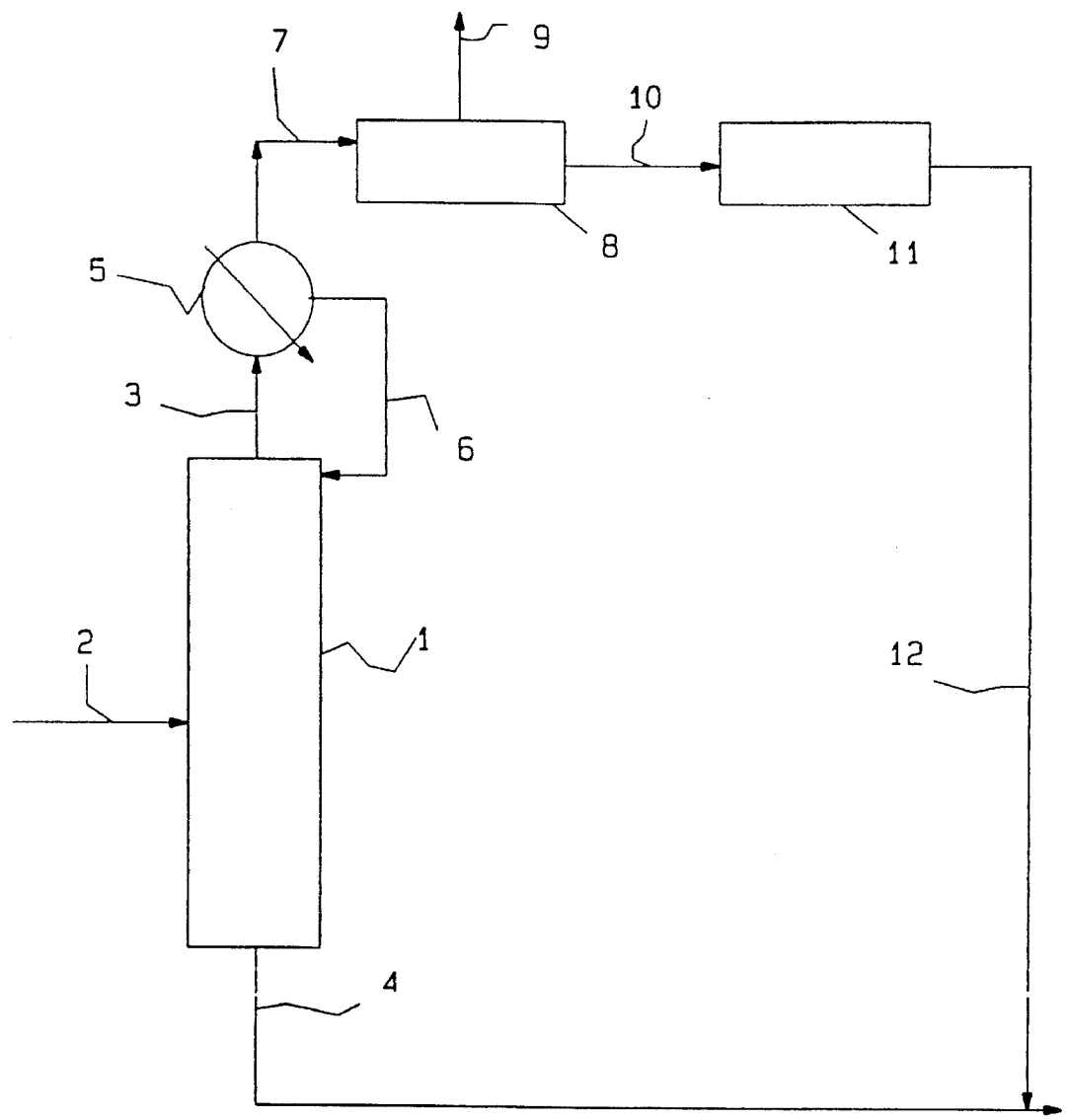
FIG. 2 illustrates a process for the purification of 1,1-dichloro-1-fluoroethane by chlorination of unsaturated hydrocarbons.

The process outlined in FIG. 2 relates to the purification of 1,1-dichloro-1-fluoroethane by chlorination of unsaturated hydrocarbons. To this end, a mixture of reaction products containing unsaturated hydrocarbons, arising from a reactor for the hydrofluorination of vinylidene chloride, is treated with chlorine in a chlorination reactor (not shown). The treated mixture of products arising from the chlorination reactor typically contains from 75 to 99 mol % of 1,1-dichloro-1-fluoroethane, from 0.01 to 20 mol % of chlorine, from 0.01 to 5 mol % of chlorinated impurities and from 0.1 to 5 mol % of hydrogen chloride, as well as 20 to 50 ppm by weight of water. This reaction mixture, denoted by the reference number (2), is introduced into a distillation column (1). The distillation column (1) is maintained at a pressure of 1 to 10 bar and the temperature at the top of the column (1) is adjusted so that the distillate leaving the column (1) via the pipe (3) contains 1,1-dichloro-1-fluoroethane. In order to avoid any formation of solid chlorine hydrates in the condenser (5), a mass content of 1,1-dichloro-1-fluoroethane of 3 to 50% in the distillate (3) is sufficient. The distillate (3) mainly comprises chlorine, hydrogen chloride, the water/1,1-dichloro-1-fluoroethane azeotrope and a small amount of excess 1,1-dichloro-1-fluoroethane. After partial condensation in the condenser (5), the condensed part of the distillate (6) is returned to the column as reflux and the non-condensed part of the distillate (7) is sent to a separation unit (8), where the chlorine and the hydrogen chloride are separated from the distillate, for example by distillation, and are removed via the pipe (9). The residual gaseous flux (10), mainly containing 1,1- dichloro-1-fluoroethane and water, is subsequently brought to a dryer (11) in order to remove the water. In the dryer (11), the gaseous flux (10) may, for example, pass through beds of adsorbent material. The gas (12), recovered at the outlet of the dryer (11), consists almost exclusively of 1,1-dichloro-1-fluoroethane. The 1,1-dichloro-1-fluoroethane, freed from the water which it has entrained out of the mixture of reaction products, may then be mixed with the liquid phase (4), recovered at the foot of the distillation column. This liquid phase (4) mainly contains 1,1-dichloro-1-fluoroethane and the chlorination products of the unsaturated hydrocarbons chlorinated in the chlorination reactor. This liquid phase (4) may be split into its various constituents in a known manner, for example by distillation, so as to recover 1,1-dichloro-1-fluoroethane in a substantially pure form. In a standard variant of the process outlined in FIG. 2, a part of the liquid phase (4) is evaporated in a distillation vessel and sent in vapour form into the column (1).

This second embodiment illustrates that the process according to the invention makes it possible to avoid any formation of hydrates between chlorine and water, and thus avoids their accumulation in cold areas of the hydrofluoroalkane production plants, in particular in the condenser at the top of a distillation column intended for the removal of unreacted chlorine from a mixture of reaction products treated with chlorine.

We claim:

1. A process for removing water from a recovered mixture of reaction products in the production of a hydrofluoroalkane, comprising:

forming a water and 1,1-dichloro-1-fluoroethane azeotrope in said mixture comprising hydrofluoroalkane and water, said azeotrope at 20° C. having a water:1,1-dichloro-1-fluoroethane molar ratio equal to (4±0.4):100 and a vapor pressure of 0.67±0.01 bar, distilling said mixture containing said azeotrope, removing said azeotrope containing water as an overhead product, and recovering said hydrofluoroalkane as a bottom product.

2. The process of claim 1, wherein the distillation is carried out in the presence of 1 to 10 times the amount of 1,1-dichloro-1-fluoroethane involved in the formation of the azeotrope.

3. The process of claim 1, wherein the hydrofluoroalkane is 1,1-dichloro-1-fluoroethane.

4. A process for removing water from a recovered mixture of reaction products in the production of a hydrofluoroalkane, comprising:

forming a water and 1-chloro-1,1-difluoroethane azeotrope in said mixture comprising hydrofluoroalkane and water, said azeotrope at 20° having a water:1-chloro-1,1-difluoroethane molar ratio equal to (1.1±0.1): 100 and a vapor pressure of 2.93±0.01 bar, distilling said mixture containing said azeotrope, removing said azeotrope containing water as an overhead product, and recovering said hydrofluoroalkane as a bottom product.

5. The process of claim 4, wherein the distillation is carried out in the presence of 1 to 10 times the amount of 1-chloro-1,1-difluoroethane involved in the formation of the azeotrope.

6. The process of claim 4, wherein the hydrofluoroalkane is 1,1-dichloro-1-fluoroethane.

7. A process for removing water from a recovered mixture of reaction products in the production of a hydrofluoroalkane, comprising:

forming a water and 1,1,1-trifluoroethane azeotrope in said mixture comprising hydrofluoroalkane and water, said azeotrope at 20° C. having a water:1,1,1-trifluoroethane molar ratio equal to (0.3±0.03):100 and a vapor pressure of 11±0.01 bar, distilling said mixture containing said azeotrope, removing said azeotrope containing water as an overhead product, and recovering said hydrofluoroalkane as a bottom product.

8. The process of claim 7, wherein the distillation is carried out in the presence of 1 to 10 times the amount of 1,1,1-trifluoroethane involved in the formation of the azeotrope.

9. The process of claim 7, wherein the hydrofluoroalkane is 1,1-dichloro-1-fluoroethane.

10. A process for removing water from a recovered mixture of reaction products in the production of a hydrofluoroalkane, comprising:

adding 1,1-dichloro-1-fluoroethane to said mixture of reaction products to form a water and 1,1-dichloro-1-fluoroethane azeotrope in said mixture of reaction products, to said azeotrope at 20° C. having a water:1,1-dichloro-1-fluoroethane molar ratio equal to (4±0.4):100 and a vapor pressure of 0.67±0.01 bar, distilling said mixture containing said azeotrope, removing said azeotrope containing water as an overhead product, and recovering said hydrofluoroalkane as a bottom product.

11. A process for removing water from a recovered mixture of reaction products in the production of a hydrofluoroalkane, comprising:

adding 1-chloro-1,1-difluoroethane to said mixture of reaction products to form a water and 1-chloro-1,1-difluoroethane azeotrope in said mixture of reaction products, said azeotrope at 20° having a water:1-chloro-1,1-difluoroethane molar ratio equal to (1.1±0.1):100 and a vapor pressure of 2.93±0.01 bar, distilling said mixture containing said azeotrope, removing said azeotrope containing water as an overhead product, and recovering said hydrofluoroalkane as a bottom product.

12. A process for removing water from a recovered mixture of reaction products in the production of a hydrofluoroalkane, comprising:

adding 1,1,1-trifluoroethane to said mixture of reaction products to form a water and 1,1,1-trifluoroethane azeotrope in said mixture of reaction products, said azeotrope at 20° C. having a water:1,1,1-trifluoroethane molar ratio equal to (0.3±0.03):100 and a vapor pressure of 11±0.01 bar, distilling said mixture containing said azeotrope, removing said azeotrope containing water as an overhead product, and recovering said hydrofluoroalkane as a bottom product.

* * * * *